United States Patent [19]

Desai

[11] 4,153,618
[45] May 8, 1979

[54] FLUORESCENT PIGMENTS
[75] Inventor: Nalin B. Desai, Bombay, India
[73] Assignee: Ciba-Geigy Corporation, Ardsley, N.Y.
[21] Appl. No.: 784,198
[22] Filed: Apr. 4, 1977
[30] Foreign Application Priority Data Apr. 22, 1976 [CH] Switzerland ............... 5045/76

[51] Int. Cl.² .......................................... C07D 311/58
[52] U.S. Cl. .................................. 260/345.2; 544/119;
544/131; 544/124; 544/146; 544/370; 544/366;
544/364; 544/135; 260/304 T; 260/307 D;
260/326.62; 260/329 F; 8/63; 8/180; 546/269;
546/194; 546/196; 546/198; 546/199; 548/327;
544/287; 544/353; 544/354; 544/355; 544/58;
544/376; 544/151; 544/368; 544/137; 544/139;
544/132
[58] Field of Search ......................... 260/345.2
[56] References Cited
U.S. PATENT DOCUMENTS

| 3,910,912 | 10/1975 | Scheuermann et al. | 260/345.2 |
| 3,920,704 | 11/1975 | Augart et al. | 260/345.2 |
| 4,005,111 | 1/1977 | Mach et al. | 260/345.2 |
| 4,007,188 | 2/1977 | Koch | 260/345.2 |

Primary Examiner—Nicky Chan

Attorney, Agent, or Firm—Prabodh I. Almaula

[57] ABSTRACT

A fluorescent pigment consisting of N-substituted iminocoumarins of the general formula I,

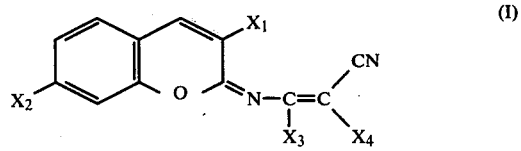

wherein $X_1$ is a cyano group, a carboxamido group or an aryl or a heteroaryl radical linked directly or through a —CO or —$SO_2$ group, $X_2$ is an amino group, hydroxy group or an alkoxy group and when it is an amino group, may carry an optionally substituted alkylene or alkylidene group bound in ortho position to the nitrogen atom and in para position with respect to the coumarin oxygen atom, $X_3$ is a hydrogen atom, a halogen atom or a cyano group and $X_4$ is a functionally converted carboxyl groups. The new dyestuffs dye polyester fiber in orange or red shades with good fastness.

5 Claims, No Drawings

FLUORESCENT PIGMENTS

The present invention relates to a new class of luminous pigments, a process for their manufacture, their use in colouring organic materials, especially the use of such pigments as are sparingly soluble in water as disperse dyestuffs for dyestuffs for dyeing and printing hydrophobic fibres, their use as organic dye lasers and as industrial products and the material dyed or printed with new pigments.

The new, fluorescent pigments, which have been found, are N-substituted iminocoumarin derivatives of the general formula I $$\text{(I)}$$

(structure with substituents $X_1$, $X_2$, $X_3$, $X_4$ on coumarin-imino system with CN group)

wherein
$X_1$ is a cyano group, a carboxamido group or an aryl or a heteroaryl radical, linked directly or through —CO or $SO_2$ group,
$X_2$ is an amino group, hydroxy group or an alkoxy group, and when it is an amino group, may carry an optionally substituted alkylene or alkylidene group bound in ortho position to the nitrogen atom and in para position to the coumarin oxygen atom,
$X_3$ is a hydrogen atom, a halogen atom or a cyano group and
$X_4$ is a functionally converted carboxyl group.

The carboxamido group $X_1$ is a group —CONHR wherein R is a hydrogen atom, an optionally substituted lower alkyl group, especially those substituted by hydroxy or acyloxy group, a cycloalkyl group, an aryl or a heteroaryl group.

The term lower referred to in this application pertaining to radicals or groups refer to those radicals or groups containing not more than 6 carbon atoms.

The aryl radicals are especially phenyl or naphthyl radicals optionally substituted by groups such as nitro or optionally substituted amino, halogen atoms e.g. fluorine, chlorine and bromine, or lower alkyl such as methyl, ethyl, n-propyl, isopropyl or n-or iso butyl radicals, or lower alkoxy, e.g. methoxy and ethoxy radicals.

The heteroaryl radicals may be mono or bicyclic heteroaryl radicals e.g. pyridyl, thienyl, furyl, triazolyl, benzimidazolyl, benzoxazolyl, benzthiazolyl, quinoxalinyl or quinazolyl radicals. Such radicals may also carry substituents such as lower alkyl, lower alkoxy radicals or halogen atoms.

The radical $X_2$ representing an amino group may also represent a mono or preferably disubstituted amino group. The substituents of the amino group are aliphatic hydrocarbon radicals especially lower alkyl radicals which may be optionally substituted for example by hydroxyl or nitrile groups, lower alkoxy groups with preferably 1 to 4 carbon atoms, acyloxy groups, phenoxy groups or halogen, such as chlorine or bromine. The following should be mentioned individually, methyl, ethyl, propyl, butyl, hexyl, β-ethylhexyl, β-hydroxyethyl or β-hydroxypropyl, γ-hydroxypropyl, ω-hydroxyhexyl, β-methoxyethyl, γ-methoxypropyl, β-ethoxyethyl, γ-ethoxypropyl, γ-isopropoxypropyl, γ-butoxypropyl, β-aminoethyl, γ-dimethylaminopropyl, γ-dibutylaminopropyl or ω-aminohexyl and the radicals of the formulae $$CH_2CH_2OCH_2CH_2OH, \quad CH_2CH_2CH_2OCH_2\underset{\underset{C_2H_5}{|}}{CH}-C_4H_9 \text{ or}$$

$$CH_2\!=\!CH\!-\!CH_2,$$

or an alkylene or alkylidene group which is bound to the benzene nucleus in orthoposition to the N-atom and in para position to the coumarin oxygen atom e.g., a group of the formula $-CH_2CH_2CH_2-$ or $$-\underset{\underset{CH_3}{|}}{\overset{}{C}}\diagdown\underset{CH_3}{\overset{CH_2-CH-}{}}\underset{CH_3}{|}$$

or other propylene or propylidene groups substituted by lower alkyl groups or hydroxy groups.

The nitrogen atom of the amino group may form part of a heteroring conjointly with the substituents present. In such cases the ring is preferably 5-membered or 6-membered and not aromatic; it can be, for example, the pyrrolidine or piperidine ring, and if this ring includes a further hetero-atom, for example, the morpholine radical or a piperazine ring which is optionally N'-substituted, especially by alkyl or acyl groups, such as the N'-acetylpiperazine radical, or a radical of the formula $$-N\diagdown\underset{CH_2-CH_2}{\overset{CH_2-CH_2}{}}\diagup SO_2$$

The group $X_4$ is preferably a carboxylic ester group especially ester of a lower alkanol such as methanol, ethanol or propanol, or a cyano group.

These new compounds of formula (I) are obtained by reacting iminocoumarins of general formula (II) with ethylene derivatives (II)    (III)

of the formula III. In formulae (II) and (III), $X_1$, $X_2$, $X_3$ and $X_4$ have the same meaning as given under formula (I) and Y represents a leaving group, such as an alkoxy especially a lower alkoxy or a cyano group or a halogen atom e.g. chlorine, bromine or a fluorine atom.

The iminocoumarins which are to be used in accordance with the invention can be obtained by the known procedure of Knoevenagel condensation between salicylaldehydes of formula IV and active methylene compounds of the formula V (IV)    (V)

where $X_1$ and $X_2$ have the meanings given earlier.
Examples of suitable salicyldehyde derivatives are:

4-Dimethylaminosalicylaldehyde, 4-diethylamino salicylaldehyde, 4-ethylamino salicylaldehyde, 4-N-ethyl-N-β-acetoxyethylsalicylaldehyde, 4-N,N-di(β-acetoxyethyl) aminosalicylaldehyde, 4-methoxysalicylaldehyde, resorcilaldehyde.

The following examples of active methylene compounds may be mentioned.

Malodinitrile, cyanoacetamide, cyanoacetaniline, p-chlorocyanoacetaniline, p-methoxycyanoacetaniline, p-nitrophenylacetaniline, p-chlorophenylacetonitrile, p-methoxyacetonitrile, 2-cyanomethylthiophene, 2-cyanomethyl benzimidazole, 2-cyanomethyloxazole, 2-cyanomethylbenztriazole, 2-cyanomethylquinazolone, 2-cyanomethylquinazoline etc.

Reaction between the iminocoumarins and the ethylene derivatives may be carried out in suitable organic solvents in the temperature range of room-temp. to 150°.

Examples of suitable solvents are hydrocarbons, such as benzene, toluene or xylenes, halogenated hydrocarbons, such as carbon tetrachloride, sym-tetrachloroethane, chlorobenzene or o-dichlorobenzene, or nitrohydrocarbons, such as nitromethane or nitrobenzene, ethers such as tetrahydrofuran, dioxane, dibutylether, esters, amides, nitriles such as ethyl acetate, dimethylformamide, acetonitrile or even dimethylsulfoxide can be used as solvent.

It is not expedient to isolate the iminocoumarins in all cases; instead the ethylene derivative is added to the reaction mixture containing the salicylaldehyde derivative and the active methylene compound.

A less general alternative procedure for the preparation of the pigments of the formula I (with $X_1=X_4=CN$, $X_2=N$ $R_1R_2$ and $X_3=H$) consists in treating m-dialkylamino phenol with two mole-equivalents of 1-chloro-2, 2-dicyanoethylene in a suitable solvent, such as chlorobenzene or tetrahydrofuran, at room-temperature.

The new pigments usually crystallize out of the reaction mixture on cooling and are easily isolated by filtration or are isolated by the removal of the solvent if necessary by steam distillation. If need be, they can be further purified by crystallization from high boiling organic solvents, such as dimethylformamide, chlorobenzene or o-dichlorobenzene. The solution of these pigments in organic solvents such as acetone, alcohol, chlorobenzene, dimethylformamide and ethyl acetate exhibit strong fluorescence in daylight and in ultraviolet light.

The new water-insoluble or sparingly soluble pigments are particularly suitable for dyeing textile material such as for example, acrylic or acrylo nitrile fibres, polyacrylonitrile fibres and copolymers of acrylonitrile and other vinyl compounds, such as acrylic esters, arylamides, vinylpyridine, vinyl chloride or vinylidene chloride, copolymers of dicyanoethylene and vinyl acetate, and of acrylonitrile block copolymers, fibres composed of polyurethanes, polyolefines, such as polypropylene modified by a base, polypropylene modified with nickel or unmodified polypropylene, cellulose triacetate and cellulose 2½-acetate and particularly fibres composed of polyamides, such as nylon 6, nylon 6,6 or nylon 12, and of aromatic polyesters, such as those of terephthalic acid and ethylene glycol or 1,4-dimethylcyclohexane, and isophthalic acid and ethylene glycol.

The new dyestuffs which are free from sulpho and quaternised nitrogen atoms are particularly suitable for dyeing textile material consisting of high molecular organic esters, such as cellulose 2½-acetate or cellulose triacetate, but particularly for dyeing or printing textile material of polymeric esters of aromatic polycarboxylic acids with polyhydric alcohols, above all polyethylene glycol terephthalate or polycyclohexanedimethylol terephthalate or textured polyesters fibres such as, for examples, DIOLEN LOFT$^R$ (Vereinigte Glazstoff-Werke), CRIMPLENE$^R$ (ICI), and SCHAPIRA$^R$ (Hoechst). The dyestuffs can, however, also be used for dyeing synthetic polyamide fibres, such as polyhexamethylene adipamide, polycaprolactam or polyamino undecanoic acid, and for dyeing polyolefines, especially polypropylene fibres. They belong to the class of the disperse dyestuffs, such as are defined, for example, in the Colour Index.

In addition, depending on the composition, they are suitable for bulk dyeing or pigmenting lacquers, oils and waxes and cellulose derivatives, especially cellulose esters, such as cellulose acetate.

The new dyestuffs can be used also for laser applications.

The following examples may be mentioned of dispersing agents of the non-ionic group which can be used with advantage: addition products of 8 mols of ethylene oxide to 1 of p-tert. -octylphenol, of 15 or 16 mols of ethylene oxide to castor oil, and of 20 mols of ethylene oxide to the alcohol $C_{16}H_{33}OH$, ethylene oxide addition products with di-phenylethyl-phenols, polyethylene oxide tert.-dodecylthioethers, polyamide polyglycol ethers or addition products of 15 or 30 mols of ethylene oxide to 1 mol of the amine $C_{12}H_{25}NH_2$ or $C_{18}H_{37}NH_2$.

The following anionic dispersing agents may be mentioned: sulphuric acid esters of alcoholic of the aliphatic series with 8 to 20 carbon atoms, of the ethylene oxide adducts of the corresponding fatty acid amides, or of alkylated phenols with 8 to 12 carbon atoms in the alkyl radical; sulphonic acid esters having alkyl radicals with 8 to 20 carbon atoms; sulphation products of unsaturated fats and oils; phosphoric acid esters having alkyl radicals with 8 to 20 carbon atoms; fatty acid soaps and also alkylarylsulphonates, condensation products of formaldehyde with naphthalenesulphonic acid and ligninsulphonates.

Suitable cationic dispersing agents are quaternary ammonium compounds containing alkyl or aralkyl radicals with 8 to 20 carbon atoms.

In addition to the dispersing agents, the dyestuff preparations can also contain organic solvents, especially solvents which boil above 100° C. and which are preferably miscible with water, such as monoalkyl glycol ethers and dialkyl glycol ethers, dioxane, dimethylformamide or dimethylacetamide, tetramethylenesulphone or dimethylsulphoxide. Dyestuff, dispersing agent and solvent can advantageously be ground with one another.

The polyester fibres are dyed from an aqueous dispersion with the dyestuffs according to the invention which are sparingly soluble in water, according to processes which are customary for polyester materials. Polyesters of aromatic polycarboxylic acids with polyhydric alcohols are preferably dyed at temperatures of above 100° C. and under pressure. The dyeing can, however, also be carried out at the boiling point of the dye bath in the presence of dyestuff carriers, for example alkali metal phenylphenolates, polychlorobenzene compounds or similar auxiliaries, or can be carried out by the padding process and subsequent hot after-treatment, for example thermofixing at 180° to 210° C. Cellulose 2½-acetate fibres are preferably dyed at temperatures of 80° to 85° C., while cellulose triacetate fibres and synthetic polyamide fibre material are dyed advantageously at the boiling point of the dye bath. When the last-mentioned kinds of fibres are dyed, the use of dyestuff carriers is superfluous.

The dyeings obtained according to the present process can be subjected to an after-treatment, for example by heating with an aquous solution of a non-ionic detergent.

The textile materials mentioned are also printed according to the customary methods, for example by printing the goods with the printing paste containing, in addition to the dyestuff and the dyeing accelerator, thickeners and customary additives, such as, for example, urea and subsequently fixing the dyestuff by steaming for 15 minutes at 100° to 130° C.

It is further possible, for example, to dye synthetic fibres, such as polyesters and polyamides, in organic solvent liquors, such as a mixture of perchloroethylene and dimethylformamide or methanol, or in perchloroethylene alone, or perchloroethylene-water emulsions.

The new iminocoumarin derivatives of the formula I which can be used as disperse dyestuffs are very well absorbed on the above-mentioned hydrophobic organic fibre material, particularly on polyethylene glycol terephthalate fibres and, on this fibre material, they yield pure, full, yellow, orange, red and bluish red dyeings with a high brilliance and fluorescence. In addition, the dyeings are very fast to washing, fulling, rubbing, perspiration, solvents, decatising, light and sublimation.

In the following examples, unless otherwise stated, parts denote parts by weight, percentages denote percentage by weight and temperatures are in degrees centigrade.

EXAMPLE 1

12.2 parts of ethoxymethylenemalodinitrile are gradually added to a boiling solution of 33.7 parts of 7-diethylamino-3-(p-nitrophenyl)-2-imino coumarin in 300 parts of chlorobenzene in about 10 minutes. The deep red brown mixture is then gently refluxed for 15 minutes. On cooling, dyestuff of the formula

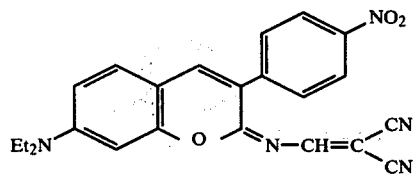

separates as red brown needles; it is filtered, washed with hexane and dried. After one crystallisation from chlorobenzene it melts at 281°-82° with slight decomposition. Its solutions in organic solvents are red with intense orange fluorescence ($\lambda_{max}$ 505 and 535 nm with $\epsilon_{max}$ 35,000 and 39,300 respectively). It dyes polyester a brilliant red shade with excellent fastness.

The iminocoumarin derivative required for above procedure is prepared as follows:

A mixture of 19.3 parts of 4-diethylaminosalicylaldehyde, 16.2 parts of p-nitrophenylacetonitrile, 0.3 part piperidine and 400 parts of ethanol is refluxed for 3 hours. On cooling iminocoumarin of the formula

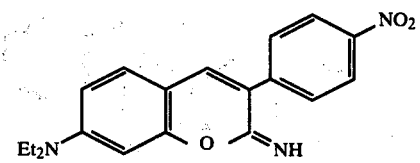

separates as shining red brown plates, m.p. 180°-85° (dec.).

PROCEDURE (B)

A mixture of 19.3 parts of 4-diethylaminosalicylaldehyde, 16.2 parts of p-nitrophenylacetonitrile, 0.3 part of piperidine and 100 parts of chlorobenzene is refluxed for 30 minutes. 12.2 Parts of ethoxymethylene malodinitrile are then added to the hot mixture and the resulting deep red brown mixture is further refluxed for 10 minutes. On cooling, the product, indentical with one described in para 1 of the procedure A, separates as brick-red needles.

EXAMPLE 2

Using 16.9 parts of ethyl 2-cyano-3-ethoxyacrylate in place of 12.2 parts of ethoxy methylenemalodinitrile in Procedure A of Example 1, one obtains the dyestuff of the formula

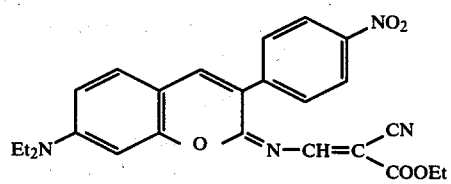

as orange red crystals; it dyes polyesters a brilliant orange shade by the thermofix procedure.

EXAMPLE 3

In place of 33.7 parts of the iminocoumarin used in Procedure A of Example 1, there are used 33.2 parts of 7-diethylamino-2-(2'-benzimidazolyl)-iminocoumarin, whereby one obtains a similar dyestuff of the formula

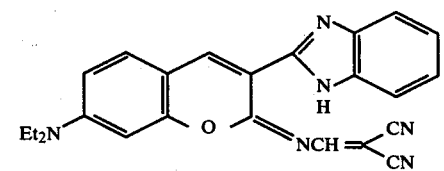

When applied by thermofix procedure from its aqueous dispersion, the dyestuff gives on polyester a fluorescent red shade of good fastness properties.

The imino-coumarin used in this Example is prepared as follows:

A mixture of 19.3 parts of 4-diethylaminosalicylaldehyde, 13.7 parts of 2-cyanomethylbenzimidazole, 0.3 part of piperidine and 300 parts of methanol is stirred at room temperature for 10 to 12 hours. The crystalline yellow precipitate of the iminocoumarin

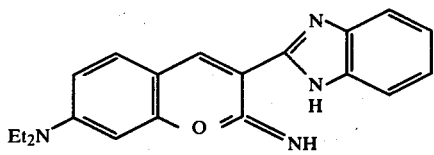

is filtered, wahsed with little methanol and dried.

EXAMPLE 4

12.2 parts of ethoxymethylenemalodinitrile are added at once to a boiling mixture of 33.5 parts of anilide of 7-diethylaminoiminocoumarin-3-carboxylic acid and 300 parts of chlorobenzene. The resulting bright red solution is simmered for 2 to 3 minutes and cooled. The separated red prisms of the dyestuff

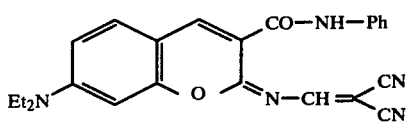

are filtered, washed with hexane and dried. It gives a bright orange shade with good fastness properties on polyester.

The iminocoumarin used in this Example is prepared by a process similar to one described for the preparation of anilide of cyanoacetic acid in place of 15.7 parts of 2-cyanomethylbenzimidazole; it is obtained as greenish yellow crystals, m.p. 200°–204°.

EXAMPLE 5

A solution of 12.8 parts of tetracyanoethylene in 150 parts of tetrahydrofuran is added gradually to a stirred mixture of 33.2 parts of 7-diethylamino-3-(2'-benzimidazolyl) iminocoumarin and 150 parts of tetrahydrofuran at room temperature. The yellow colour of the mixture thereby changes to violet brown and violet brown crystals with metallic luster soon begin to separate. The mixture is stirred at room temperature for one-half hour and the violet brown crystalline product, which corresponds to the structure

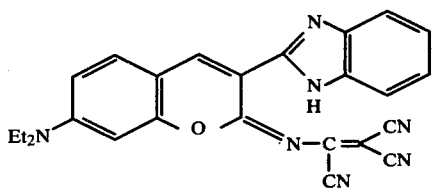

is filtered, washed with small amount of tetrahydrofuran and dried.

It gives on polyester a violet shade.

EXAMPLE 6

(i) 10.8 parts of ethyl chloroformate are added gradually to a solution of 13.9 parts of m-nitrophenol in 40 parts of water containing 4 parts of sodium hydroxide at 20°–22°. After the addition is over the mixture is stirred at 20°–22° for 30 minutes and the precipitated colourless crystalline product

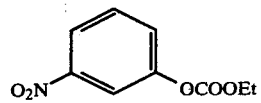

is filtered, washed neutral and dried; after one recrystallization from alcohol it melts at 53°–54°.

(ii) 21.1 Parts of the above ester are dissolved in 100 parts of alcohol and reduced catalytically at atmospheric pressure in presence of 5% palladium on charcoal. After filtering off the catalyst, the reduced product

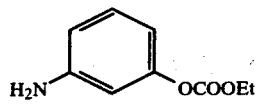

is recovered from the filtrate as colourless viscous oil and is used for the next step without further purification.

(iii) A mixture of 18.1 parts of the above reduced product, 100 parts of absolute ethanol and 8 parts of Raney nickel catalyst is refluxed with stirring for 7 hours. After cooling, the catalyst is filtered and the crude secondary amine

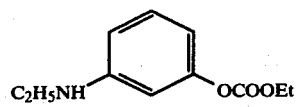

is recovered from alcohol filtrate and purified by fractional distillation under high vacuum (b.p. 175°–80°/1 mm).

(iv) 8.0 Parts of liquified ethylene oxide are added to a mixture of 21.0 parts of the above secondary amine, 50 parts of acetic acid and 50 parts of water with stirring at room-temperature. The mixture is then stirred in a closed vessel at room temperature until thin layer chromatogram of the reaction mixture indicates completion of the reaction (3 to 5 hours). The solvent is then removed completely from the reaction mixture by evaporation under reduced pressure and the crude product

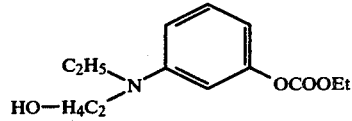

obtained as viscous oil is heated with 30 parts of acetic anhydride on a boiling water-bath for 1 hour. Excess acetic anhydride and acetic acid formed are then removed by evaporation under reduced pressure and the crude acetyl derivative obtained as clean viscous oil

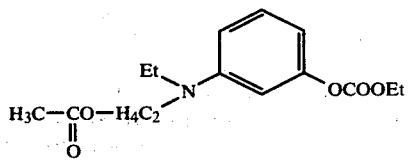

is used for the next step without further purification.

(v) 29.5 Parts of the above acetyl derivative are added to a solution of 23.0 parts of phosphorus oxychloride in 30 parts of dimethylformamide at room temperature. The temperature of the mixture is then raised to 60°-65° and it is stirred at this temperature for 5 hours. It is then poured into 500 parts of cold water and the resulting aqueous mixture is neutralized to pH 5-6 by addition of sodium acetate, whereby the formyl derivative

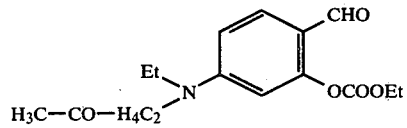

separates as an oil. It is separated from the aqueous mixture by extraction with chloroform and is used without further purification for the next step.

(vi) 25.0 Volume parts of 10 N caustic potash solution are added to a solution of 32.3 parts of the above aldehyde in 300 parts of methanol and the mixture is refluxed on boiling water-bath for 30 minutes. After cooling 25.0 parts of conc. hydrochloric acid are added to the mixture and the precipitated potassium chloride is filtered off. From the filtrate, solvent is removed completely and the hydrolyzed product

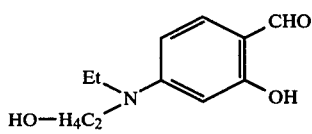

is extracted from the residue with 150 parts of boiling chlorobenzene. The chlorobenzene extract is then treated with 16.2 parts of p-nitrophenyl acetonitrile, and 9.3 parts of piperidine and the mixture is then refluxed for 15 minutes. The resulting yellow-brown mixture containing the iminocoumarin derivative

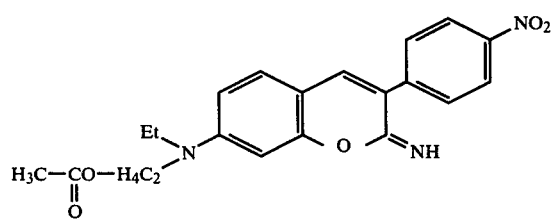

is treated with 12.2 parts of ethoxymethylene malodinitrile and the resulting deep red solution is simmered for 1-2 minutes. On cooling, the dyestuff of the formula

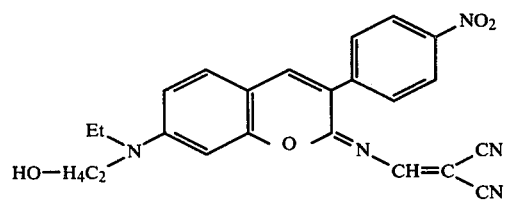

separates out as brick-red crystals; it is filtered, washed with petroleum ether and dried. It dyes polyester a brilliant, fluorescent orange shade.

EXAMPLE 7

A mixture of 5.0 parts of the dyestuff of Example 6 and 25.0 parts of acetic anhydride is heated on boiling water bath for 1 hour and poured into 250 parts of cold water. The brick red precipitate of the dyestuff

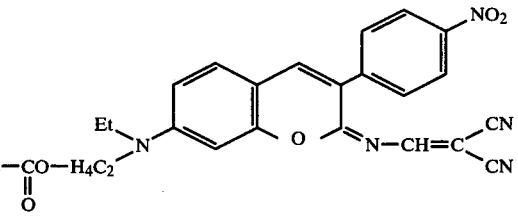

that separates on standing is filtered, washed and dried. It also dyes polyester, an attractive, fluorescent, orange shade.

EXAMPLE 8

(i) A mixture of 18.1 parts of ethyl m-aminophenoxyformate and 8.5 parts of benzylbromide is stirred on a boiling water bath for 30 minutes. After cooling the mixture is diluted with 150 parts of benzene and stirred until the precipitation of the hydrobromide of ethyl m-aminophenoxyformate is complete. The crystalline precipitate is filtered off and the secondary amine

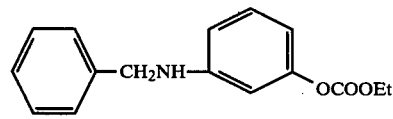

is recovered from the filtrate as colourless viscous oil.

(ii) 8.0 Parts of liquefied ethyleneoxide are added to a mixture of 27.1 parts of the above secondary amine, 100 parts of acetic acid and 100 parts of water and the mixture is stirred in a closed vessel for 22 to 24 hours. Excess ethyleneoxide and the solvents are then removed by evaporation under reduced pressure from the reaction mixture and the residual tertiary amine

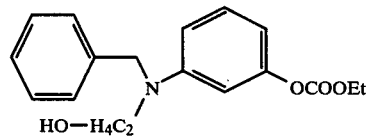

is heated with 30 parts of acetic anhydride on a boiling water-bath for 1 hour. After removing excess acetic anhydride and acetic acid formed from the reaction mixture by evaporation under reduced pressure, 35.7 parts of the resulting acetyl derivative

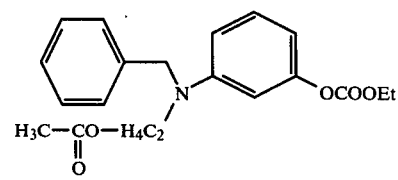

are formylated with a mixture of 23.0 parts of phosphorus oxychloride and 30 parts of dimethylformamide as described in Example 6. The crude formyl derivative

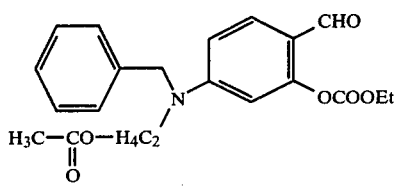

obtained as viscous, brownish oil is used without further purification.

(iii) A solution of 38.5 parts of the above aldehyde in 300 parts of methanol is refluxed with 25.0 volume parts of 10 N caustic potash for 30 minutes. After cooling 25.0 parts of conc. hydrochloric acid are added to the mixture and the precipitated potassium chloride is filtered off. From the filtrate, methanol is removed completely and the hydrolysed product

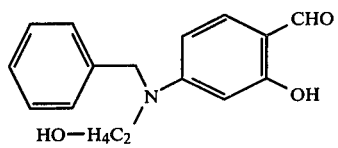

is extracted with 150 parts of boiling chlorobenzene. Chlorobenzene extract is then treated with 16.2 parts of p-nitrophenylacetonitrile in presence of 0.3 parts of piperidine and refluxed for 15 minutes to yield a yellow brown solution of the iminocoumarin.

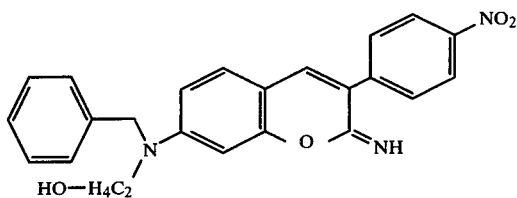

The hot solution of the latter is then treated with 12.2 parts of ethoxymethylenemalodinitrile and the resulting deep red solution on cooling yields the dyestuff of the formula

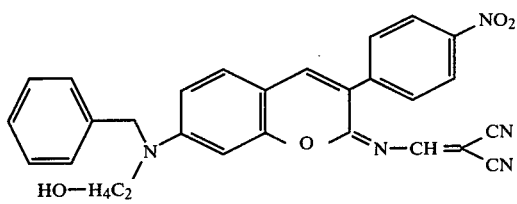

as brick-red crystals; it also gives fluorescent orange shade on polyester.

EXAMPLE 9

A mixture of 5.0 parts of the dyestuff of Example 8 and 20 parts of benzoylchloride is refluxed with stirring for 5 minutes. On cooling, dyestuff of the formula

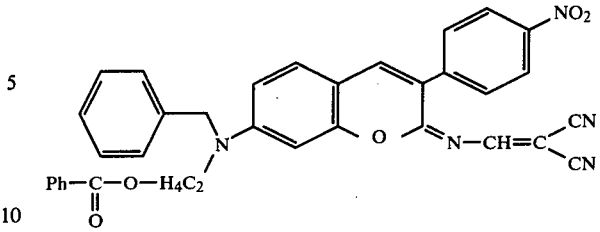

separates as brick-red crystals; it is filtered, washed with ether and dried. It also gives a deep, brilliant orange red on polyester.

EXAMPLE 10

16.0 Parts of liquefied ethyleneoxide are added to a mixture of 18.1 parts of ethyl m-aminophenoxyformate, 50.0 parts of acetic acid and 50.0 parts of water at room temperature and the mixture is stirred in a closed vessel for 16 hours. Solvent is then completely removed and the residual oily product

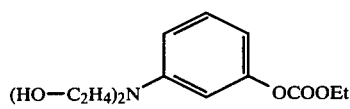

is acetylated by heating with 50.0 parts of acetic anhydride on boiling water-bath for 30 minutes. After stirring off excess acetic anhydride and acetic acid from the reaction mixture, the bisacetylated product

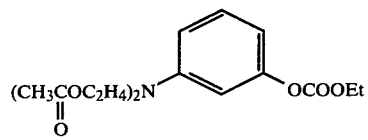

is formylated as described in Example 6. 38.1 Parts of the aldehyde

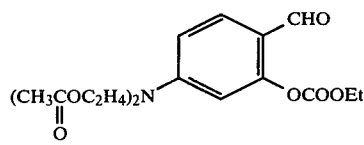

are then hydrolyzed by boiling its methanolic solution with 30 vol.parts of 10 N caustic potash solution. The hydrolized product

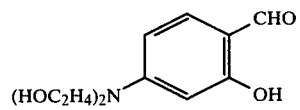

is taken up in 150 parts of chlorobenzene and treated sucessively with 16.2 parts of p-nitrophenylacetonitrile (in presence of 0.3 parts piperidine) and 12.2 parts of ethoxymethylenemalodinitrile, as described in para (vi) of Example 6, to yield the dyestuff of the formula

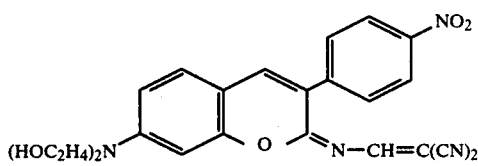

as deep violet red crystals.

EXAMPLE 11

A mixture of 10.0 parts of the dyestuff of Example 10, 30 parts of acetic anhydride and 30 parts of acetic acid is heated on boiling water-bath for 30 minutes. On cooling, the dyestuff of formula

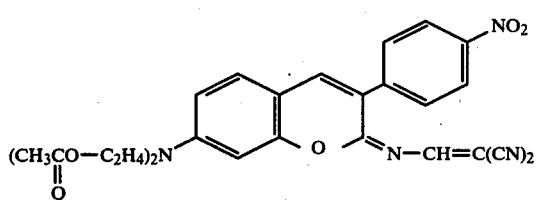

separates as red crystals; it is filtered, washed with little acetic acid and dried. It gives a brilliant orange red shade on polyester.

EXAMPLE 12

(i) A mixture of 18.1 parts of ethyl m-aminophenoxyformate and 8.5 parts of ethyl 3-bromopropionate on a boiling water-bath for 40 minutes. After cooling, the reaction mixture is stirred with 100 parts of benzene and the precipitated hydrobromide of ethyl m-aminophenoxyformate is filtered off. Removal of solvent from the filtrate gives the secondary amine of the formula

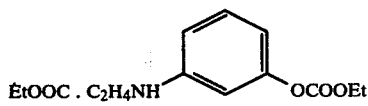

as colourless, viscous oil.

(ii) 8.0 Parts of ethyleneoxide are added to a mixture of 28.1 parts of the above secondary amine, 100 parts of acetic acid and 100 parts of water and the mixture is stirred in a closed vessel at room temperature for 16 hours. On removing the solvent from the reaction mixture, the hydroxy ethylated product

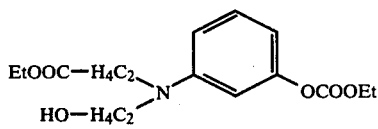

is obtained as colourless viscous oil, which is then heated with 50.0 parts of acetic anhydride to yield the acetyl derivative

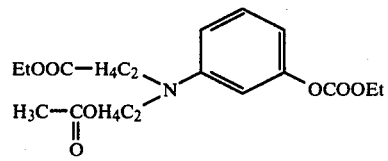

(iii) 36.7 Parts of the above tertiary amine are added to a mixture of 23.0 parts of phosphorusoxychloride and 30.0 parts of dimethylformamide. The mixture is heated to 60°-65° with stirring for 5 hours and worked up as described in example 6 to yield the formyl derivative of the structure

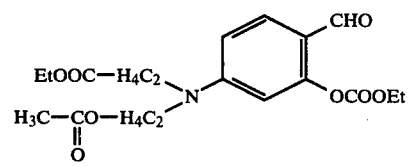

as viscous oil.

(iv) A solution of the above aldehyde in 300 parts of methanol is refluxed with 30.0 vol.parts of 10 N caustic potash for 30 minutes. After cooling, the mixture is treated with 30.0 parts of concentrated hydrochloric acid, precipitated potassium chloride is filtered off and the residue of the hydrolyzed product

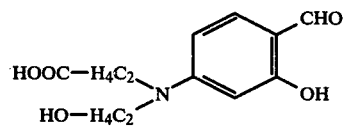

obtained after removal of the solvent form the filtrate is extracted with 150 parts of boiling chlorobenzene. Chlorobenzene extract is then refluxed with 15.7 parts of 2-cyanomethyl benzimidazole, 0.3 part of piperidine for 15 minutes and the resulting solution containing the iminocoumarin derivative

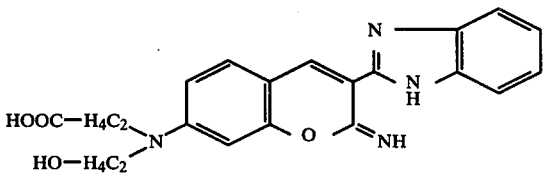

is treated with 12.2 parts of ethoxymethylenemalodinitrile and refluxed further for 5 minutes. On cooling, the dyestuff of the structure

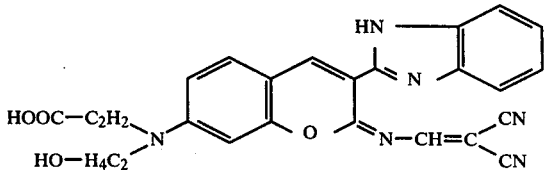

separates out as deep red crystals; it gives bright red dyeings on nylon and polyester.

EXAMPLE 13

(i) A mixture of 18.1 parts of ethyl m-aminophenoxyformate, 6.0 parts of acrylonitrile and 20 parts of phenol is heated in a closed vessel at 100°–105° for 20 hours. Phenol is removed from the reaction mixture by distillation under high vacuum and the residual monocyanoethylated product

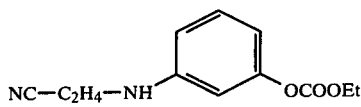

is used for the next step without any purification.

(ii) A mixture of 23.4 parts of the secondary amine described above, 8.0 parts of liquefied ethyleneoxide, 100 parts of acetic acid and 100 parts of water is stirred in a closed vessel at room temperature for 5 hours. The hydroxyethylated product

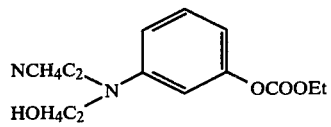

recovered from the reaction mixture by the complete removal of solvent is then acetylated by heating with 50 ml of acetic anhydride on boiling water-bath for 30 minutes. 32.0 Parts of the acetyl derivative

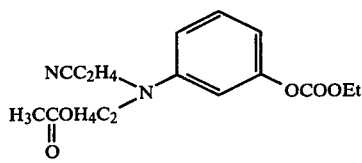

are then formylated according to the procedure described in example 6 and the formyl derivative

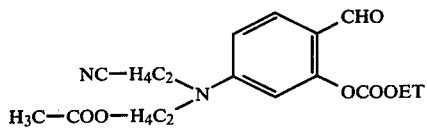

is hydrolysed according to procedure used in example 6 to yield the salicylaldehyde derivative

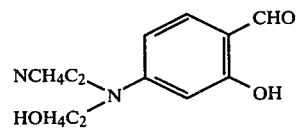

solution in 150 parts of chlorobenzene. The latter is then treated with 16.2 parts of p-nitrophenylacetonitrile 10.3 parts of piperidine and refluxed for 15 minutes. The resulting solution of iminocoumarin

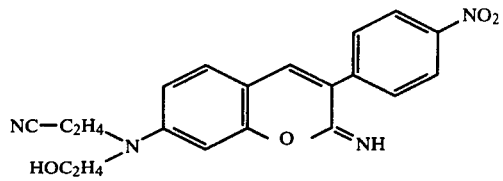

is treated with 12.2 parts of ethoxy of ethoxymethylene malodinitrile, in usual manner, to yield the dyestuff of the structure

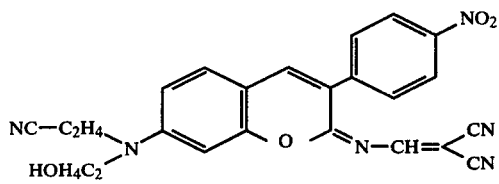

as brick-red crystals. It gives a bright yellow-orange shade on polyester.

EXAMPLE 14

A mixture of 19.3 parts of 4-diethylaminosalicylaldehyde, 12.3 parts of 2-thienylacetonitrile, 0.3 part piperidine and 100 parts of chlorobenzene is refluxed for 12 minutes. The hot solution, containing the iminocoumarin derivative

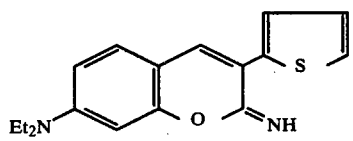

is treated with 12.2 parts of ethoxymethylenemalodinitrile and the resulting deep reddish violet solution is simmered for 2 to 3 minutes. On cooling, dyestuff of the formula

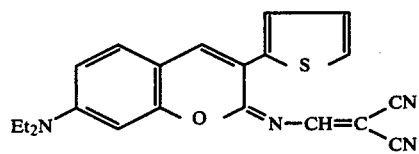

separates as dark violet crystals. It gives a bright red shade on polyester.

EXAMPLE 15

Using 11.8 parts of 3-pyridylacetonitrile, in place of 2-thienylacetonitrile in the above procedure (Example 14), one obtains the dyestuff of the formula

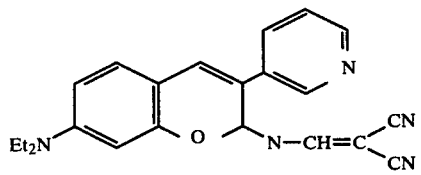

It dyes polyester an attractive fluorescent, pink shade.

EXAMPLE 16

Using 11.8 parts of 2-pyridylacetonitrile in place of 2-thienylacetonitrile and 16.9 parts of ethyl 2-cyano-3-ethoxyacrylate in place of 12.2 parts of ethoxymethylenemalodinitrile, one obtains the dyestuff of the formula

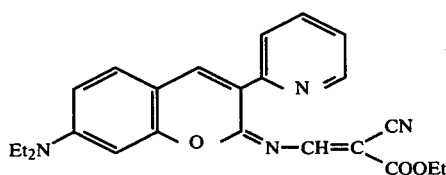

as red crystals. It gives a fluorescent orange-red shade on polyester.

EXAMPLE 17

If in place of 2-thienylacetonitrile in the procedure of example 14, there are used 15.2 parts of p-chlorobenzylcyanide, one obtains the dyestuff of formula

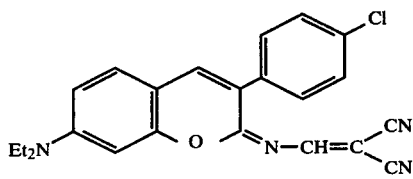

as brick-red crystals. It dyes polyester an attractive, fluorescent red shade.

EXAMPLE 18

A mixture of 15.2 parts of 4-methoxy salicylaldehyde, 15.7 parts of 2-cyanomethyl benzimidazole, 0.3 part of piperidine and 150 parts of methanol is stirred at room temperature for 16 hours. The crystalline, greenish-yellow precipitate of iminocoumarin

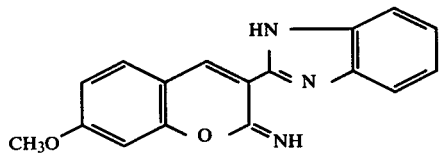

is filtered, washed with methanol and dried.

EXAMPLE 19

12.2 Parts of ethoxymethylenemalodinitrile are added to a boiling mixture of 29.1 parts of the iminocoumarin described above and 100 parts of chlorobenzene. The resulting clear red-brown solution is simmered for 5 minutes. On cooling, dyestuff of the formula

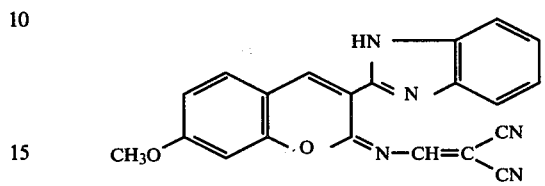

separates as orange-red prisms. It gives a full reddish-yellow shade on polyester.

EXAMPLE 20

A solution of 14.7 parts of 1,1-dichloro-2,2-dicyanoethylene in 100 parts of chlorobenzene is added to a boiling solution of 33.7 parts of 7-diethylamino-3-(p-nitrophenyl)-2-iminocoumarin in 100 parts of chlorobenzene and the deep red mixture is refluxed for 5 minutes. On cooling, the dyestuff of the formula

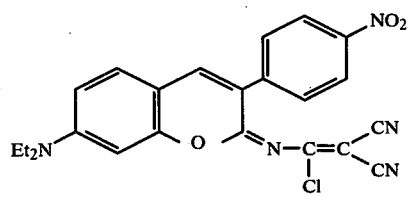

separates as deep red crystals. It is filtered, washed repeatedly with methanol and recrystallized from chlorobenzene to free it from yellow impurities. It also dyes polyester a brilliant orange shade.

Examples of other dyes prepared by similar procedures are given in the following table.

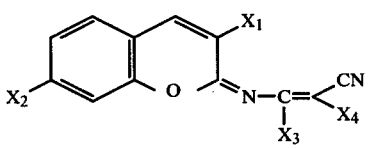

| Example | $X_1$ | $X_2$ | $X_3$ | $X_4$ | Shade |
|---|---|---|---|---|---|
| 21 | ![benzoxazole] | N(Et)$_2$ | H | CN | Red |
| 22 | ![benzothiazole] | " | " | " | Red |
| 23 | —CONHC$_3$H$_6$OH | " | " | " | Orange |
| 24 | —CONHC$_3$H$_6$OAc | N(C$_2$H$_4$OAc)$_2$ | " | " | Orange |

-continued structure: chromene with $X_2$ on benzene ring, $=CH-C(X_1)=$ linked via $-C(=N-)-$ to $C(X_3)(X_4)$ with CN group

| Example | $X_1$ | $X_2$ | $X_3$ | $X_4$ | Shade |
|---|---|---|---|---|---|
| 25 | —CO—C$_6$H$_4$—NO$_2$ (p) | N(Et)$_2$ | " | " | Orange-yellow |
| 26 | —C$_6$H$_4$—OCH$_3$ (p) | N(CH$_3$)$_2$ | " | " | Red |
| 27 | 2-NO$_2$-thienyl | N(Et)$_2$ | " | " | Bluish-red |
| 28 | 2-NO$_2$-furyl | " | " | " | Bluish-red |
| 29 | 4-pyridyl | " | " | " | Orange-red |
| 30 | 2-(benzimidazolyl) | —N(Et)(C$_2$H$_4$OAc) | " | " | Red |
| 31 | " | —N(CH$_2$Ph)(C$_2$H$_4$OAc) | " | " | Red |
| 32 | —C$_6$H$_4$—NO$_2$ (p) | —N(Et)(C$_3$H$_4$OAc) | " | " | Orange-red |
| 33 | " | —N(CH$_2$Ph)(C$_2$H$_4$COOCH$_3$) | " | " | Orange-red |
| 34 | " | —N(Et)(C$_2$H$_4$—OCH$_3$) | " | " | Orange-red |
| 35 | " | —N(Et)(C$_2$H$_4$OCOPh) | " | " | Orange-red |
| 36 | " | " | " | COOC$_2$H$_5$ | Orange-red |
| 37 | " | —N(Et)(C$_2$H$_4$OCONHPh) | " | CN | Orange-red |
| 38 | —CONH—C$_6$H$_4$—OCH$_3$ (p) | N(Et)$_2$ | " | " | Orange |
| 39 | —CONH—C$_6$H$_4$—NO$_2$ (p) | " | " | " | Orange |
| 40 | —CONH—C$_6$H$_4$—NO$_2$ (m) | " | " | " | Orange |
| 41 | —CONH—C$_6$H$_4$—NHAc (p) | " | " | " | Orange |

-continued

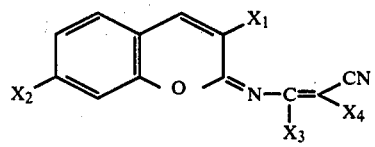

| Example | X₁ | X₂ | X₃ | X₄ | Shade |
|---|---|---|---|---|---|
| 42 | —CONH—C₆H₄—NHAc (3-NHAc) | " | " | " | Orange |
| 43 | —CONH—C₆H₄—Cl (4-Cl) | " | " | COOC₂H₅ | Orange |
| 44 | —CONH—C₆H₄—Cl (3-Cl) | " | " | " | Orange |
| 45 | 2-(acetamidinyl)benzamido group | " | " | " | Red |
| 46 | 3-pyridyl | N(CH₃)₂ | " | CN | Pink |
| 47 | 1-methylpyrrol-2-yl | N(Et)₂ | " | " | Red |
| 48 | 5-chlorobenzoxazol-2-yl | " | " | " | Red |
| 49 | benzoxazol-2-yl | OEt | " | " | Yellow |
| 50 | 5-chlorobenzoxazol-2-yl | OCH₃ | " | " | Yellow |
| 51 | benzothiazol-2-yl | N(Et)₂ | CN | " | Violet |
| 52 | " | " | Cl | " | Red |
| 53 | —SO₂Ph | " | " | " | Orange |
| 54 | —CO—C₆H₄—NO₂ (4-NO₂) | " | " | " | Yellow-orange |

EXAMPLE 55

A solution of 11.2 parts of 1-chloro-2,2-dicyanoethylene in 50 parts of chlorobenzene is added to a solution of 25.0 parts of m-diethylaminophenol in 150 parts of chlorobenzene at room temperature in about 10 minutes. The resulting deep red-brown mixture is stirred at room temperature for 1 hour more. Solvent is then removed from the reaction mixture by steam distillation when the product

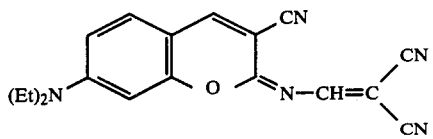

separates as clear red-brown crystalline precipitate. It is filtered, washed and dried. It dyes polyester a fluorescent orange shade.

What I claim is:

1. A fluorescent pigment consisting of N-substituted iminocoumarin of the general formula I,

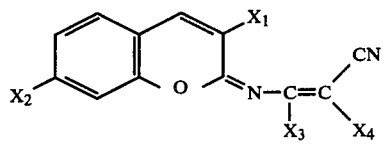

wherein
- $X_1$ is an unsubstituted phenyl or naphthyl, or phenyl or naphthyl substituted by nitro, amino, halogen, lower alkyl or lower alkoxy, linked directly or through a —CO or —SO$_2$ group;
- $X_2$ is (a) an amino group which is unsubstituted or mono- or di-substituted by lower alkyl or lower alkyl substituted by hydroxyl, nitrile, lower alkoxy, phenyl, phenylaminocarbonyloxy, phenoxy, halogen, lower alkoxycarbonyl, or acyloxy selected from benzoyloxy or acetyloxy; or by radicals —CH$_2$CH$_2$OCH$_2$CH$_2$OH, $$-CH_2CH_2OCH_2\overset{\overset{\displaystyle C_2H_5}{|}}{CH}-C_4H_9,$$

or —CH$_2$=CH—CH$_2$; or
  (b) a hydroxy group or an alkoxy group;
- $X_3$ is a hydrogen atom, a halogen atom or a cyano group and
- $X_4$ is a carboxylic acid group which has been esterified by lower alkanol, or a cyano group.

2. An iminocoumarin compound according to claim 1 characterised in that $X_2$ is a dialkylamino group and $X_1$, $X_3$ and $X_4$ have the meanings given under claim 1.

3. An iminocoumarin compound according to claim 1 characterised in that $X_3$ is a hydrogen atom or a cyano group.

4. An iminocoumarin compound according to claim 1 characterised in that the group $X_4$ is a cyano group.

5. The dyestuff according to claim 1 of the formula

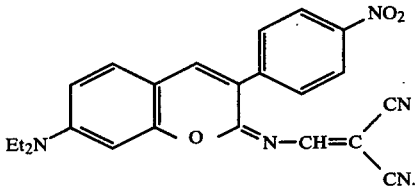

* * * * *